United States Patent [19]

Poss et al.

[11] Patent Number: 5,212,177
[45] Date of Patent: May 18, 1993

[54] INDOLE AND BENZIMIDAZOLE-SUBSTITUTED DIHYDROPYRIMIDINE DERIVATIVES

[75] Inventors: Michael A. Poss, Lawrenceville, N.J.; Karnail S. Atwal, Newtown, Pa.

[73] Assignee: E. R. Squibb & Sons, Inc., Princeton, N.J.

[21] Appl. No.: 808,350

[22] Filed: Dec. 16, 1991

[51] Int. Cl.[5] .............. A61K 31/505; A61K 31/675; C07D 211/26; C07D 211/56; C07D 403/06; C07D 487/02

[52] U.S. Cl. .................... 514/259; 514/81; 514/86; 514/215; 514/258; 514/260; 514/269; 514/272; 514/274; 514/275; 540/521; 544/231; 544/232; 544/243; 544/244; 544/278; 544/279; 544/280; 544/284; 544/286; 544/292; 544/295; 544/310; 544/316; 544/318; 544/319; 544/321; 544/322

[58] Field of Search .............. 544/231, 278-280, 544/232, 292, 295, 284, 316, 318, 322, 243, 244, 286, 310, 319, 321; 514/258, 259, 81, 86, 260, 269, 272, 274, 275; 540/521

[56] References Cited

U.S. PATENT DOCUMENTS

| | | | |
|---|---|---|---|
| 4,340,598 | 7/1982 | Furukawa et al. | 548/337 |
| 4,355,040 | 10/1982 | Furukawa et al. | 548/337 |
| 4,582,847 | 4/1986 | Furukawa et al. | 514/400 |
| 4,812,462 | 3/1989 | Blankley et al. | 546/118 |
| 4,816,463 | 3/1989 | Blankley et al. | 514/293 |
| 4,820,843 | 4/1989 | Aldrich et al. | 548/282 |
| 4,855,301 | 8/1989 | Atwal et al. | 514/269 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |

FOREIGN PATENT DOCUMENTS

| | | |
|---|---|---|
| 253310 | 1/1988 | European Pat. Off. |
| 323841 | 7/1989 | European Pat. Off. |
| 324377 | 7/1989 | European Pat. Off. |
| 411766 | 2/1991 | European Pat. Off. |

OTHER PUBLICATIONS

Karnail S. Atwal et al., "Substituted 1,4-Dihydropyrimidines, 3.Synthesis of Selectively Functionalized 2-Hetero-1,4-dihydropyrimidines", *J. Org. Chem*, 1989, 54, pp. 5898-5907.

Primary Examiner—Cecilia Tsang
Attorney, Agent, or Firm—Ellen K. Park

[57] ABSTRACT

Novel compounds having the formula

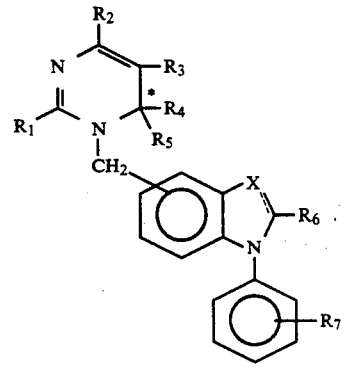

and its isomer

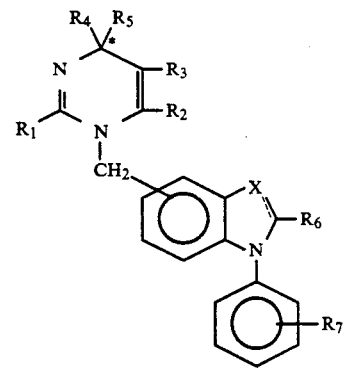

wherein $R_1$, $R_2$, $R_3$, $R_4$, $R_5$, $R_6$, $R_7$ and X are as defined herein. These compounds inhibit the action of angiotensin II and are useful, therefore, for example, an antihypertensive agents.

10 Claims, No Drawings

INDOLE AND BENZIMIDAZOLE-SUBSTITUTED DIHYDROPYRIMIDINE DERIVATIVES

FIELD OF THE INVENTION

The present invention relates to novel substituted dihydropyrimidine derivatives which are useful as antihypertensive agents.

SUMMARY OF THE INVENTION

In accordance with the present invention, novel compounds which inhibit the action of the hormone Angiotensin II are disclosed. These compounds are of the general formula

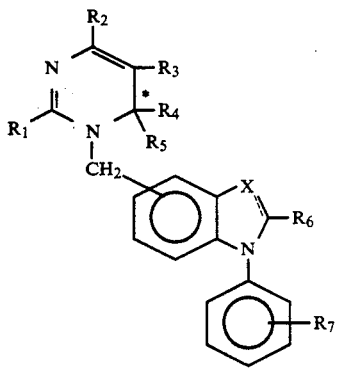

I and its isomer

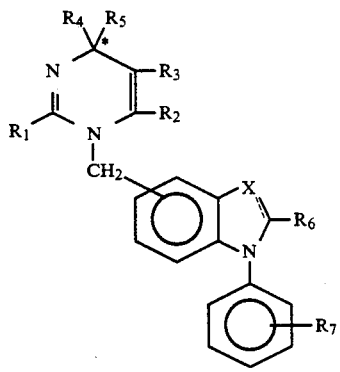

I' and pharmaceutically acceptable salts thereof; wherein

X is —N— or

when X is —N—, the double bond is always present;

$R_1$ is alkyl, alkenyl or alkynyl or an alkyl, alkenyl or alkynyl group substituted with F or —$CO_2R_8$; cycloalkyl; (cycloalkyl)alkyl of 4 to 10 carbon atoms; (cycloalkyl)alkenyl or (cycloalkyl)alkynyl of 5 to 10 carbon atoms; —$NR_{11}R_{12}$; —$(CH_2)_mZ(CH_2)_nR_{14}$; benzyl or benzyl substituted with 1 or 2 halogens, alkoxy of 1 to 4 carbon atoms, alkyl of 1 to 4 carbon atoms, haloalkyl or nitro; —$SR_{15}$; or —$OR_{15}$;

$R_2$ is halogen, —CN, —$OR_{15}$, —$SR_{15}$, —$COR_{15}$, $R_{16}$, ($R_{16}O$)alkyl, ($R_{16}S$)alkyl, —$CO_2R_{17}$ or (substituted amino)alkyl;

$R_3$ is —CN, —$NO_2$,

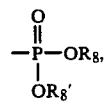

—$CONR_{11}R_{12}$, ($R_{15}OCO$)alkyl, ($R_{16}O$)alkyl, ($R_{16}S$)alkyl, ($R_{16}CO$)alkyl, —$CO_2R_{17}$, $R_{18}$, —$CO_{18}$, —$SO_2R_{18}$ or ($R_{18}OC$)alkyl; or $R_2$ and $R_3$ taken together are $$-\overset{O}{\underset{\|}{C}}-O(CH_2)_p-CH_2-, -\overset{O}{\underset{\|}{C}}-S(CH_2)_p-CH_2- \text{ or}$$

$$-\overset{O}{\underset{\|}{C}}-\underset{\underset{R_{16}}{|}}{N}(CH_2)_p-CH_2-$$

to form a 5- to 7-membered ring with the carbon atoms to which they are attached; or $R_2$ and $R_3$ taken together with the carbon atoms to which they are attached form an aryl or heterocyclo group;

$R_4$ and $R_5$ are independently selected from hydrogen, alkyl, alkenyl, alkynyl, aryl, arylalkyl, cycloalkyl, (cycloalkyl)alkyl, heterocyclo, (heterocyclo)alkyl, haloalkyl or —$CO_2R_8$; or $R_4$ and $R_5$ taken together with the carbon atom to which they are attached form a 5- to 7-membered carbocyclic ring which may have another 5- to 7-membered ring fused thereto; or $R_4$ and $R_5$ together with the carbon atom to which they are attached form a carbonyl or a thiocarbonyl group;

$R_6$ and $R_6'$ are independently selected from hydrogen, alkyl, aryl, cycloalkyl, arylalkyl, haloalkyl, —$CO_2R_8$, —$NHSO_2CF_3$, —$\overset{O}{\underset{\|}{C}}(OH)_2$, —$SO_3H$, —$C(CF_3)_2OH$,

—$OP(OH)_2$, —$PO_3H$, —$NHP(OH)_2$, —$CONHNHSO_2CF_3$,

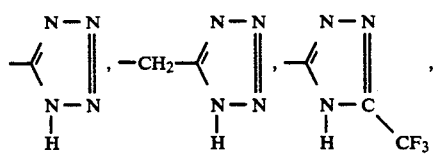

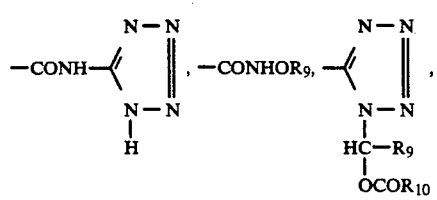

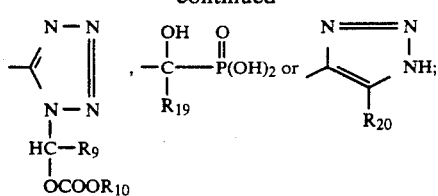

$R_7$ is an acid moiety such as hydrogen,

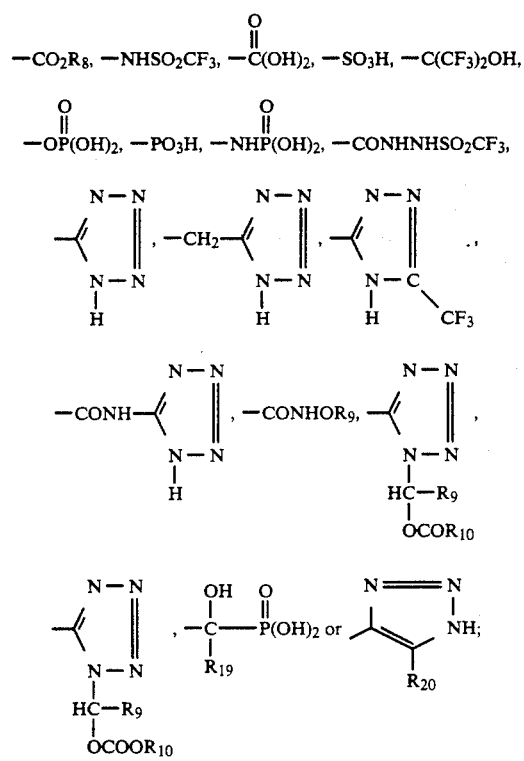

$R_8$ and $R_8'$ are independently hydrogen, alkyl, perfluoroalkyl of 1 to 8 carbon atoms, cycloalkyl of 3 to 6 carbon atoms, phenyl, benzyl,

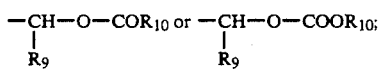

$R_9$ is hydrogen, alkyl, aryl, arylalkyl or cycloalkyl;
$R_{10}$ is alkyl, aryl, alkylaryl, arylalkyl or cycloalkyl;
$R_{11}$ and $R_{12}$ are independently hydrogen, alkyl of 1 to 6 carbon atoms, benzyl, α-methylbenzyl, or taken together with the nitrogen atom to which they are attached form a ring of the formula

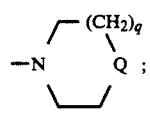

$R_{13}$ is hydrogen, alkyl of 1 to 6 carbon atoms, cycloalkyl of 3 to 6 carbon atoms, phenyl or benzyl;
$R_{14}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or $-CO_2R_8$;

$R_{15}$ is alkyl, alkenyl, alkynyl, aryl, arylalkyl, cycloalkyl, (cycloalkyl)alkyl, heterocyclo, (heterocyclo)alkyl or haloalkyl;

$R_{16}$ is hydrogen, alkyl, alkenyl, alkynyl, aryl, arylalkyl, cycloalkyl, (cycloalkyl)alkyl, heterocyclo, (heterocyclo)alkyl or haloalkyl;

$R_{17}$ is hydrogen, alkyl, alkenyl, alkynyl, perfluoroalkyl of 1 to 8 carbon atoms, cycloalkyl, aryl, arylalkyl, (cycloalkyl)alkyl, heterocyclo, (heterocyclo)alkyl, haloalkyl,

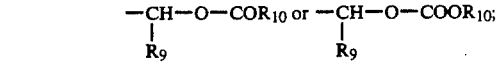

$R_{18}$ is aminoalkyl, (substituted amino)alkyl; or $R_{16}$;
$R_{19}$ is hydrogen, alkyl of 1 to 5 carbon atoms or phenyl;
$R_{20}$ is $-CN$, $-NO_2$ or $-CO_2R_8$;
Q is $-CH_2$, $-O-$, or $-NR_9$;
Z is $-O-$, $-S-$ or $-NR_{13}$;
m is an integer of 1 to 5;
n is an integer of 1 to 5;
p is 0, or the integer 1 or 2; and
q is 0, or the integer 1.

DETAILED DESCRIPTION OF THE INVENTION

The present invention relates to the compounds of formula I and I' and to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "haloalkyl" refers to such alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc., trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. The aryl group is attached by way of an available carbon atom or is fused when $R_2$ and $R_3$ taken together with the carbon atoms to which they are attached form the aryl ring. Preferred aryl groups are phenyl and monosubstituted phenyl and phenyl is most preferred.

The term "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms. The heterocyclo ring is attached by way of an available carbon atom or is fused when $R_2$ and $R_3$ taken together with the carbon atoms to Which they are attached, form the heterocyclic ring. Preferred monocyclic heterocyclo groups include 2- and 3-thienyl, 2- and 3-furyl, 2-, 3- and 4-pyridyl, and imidazolyl. The heterocycle may also have a substituent selected from alkyl of 1 to 4 carbons, carboxy, alkoxy of 1 to 4 carbons and alkylthio of 1 to 4 carbons on an available carbon. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranyl. Preferred fused heterocycles include thienyl, furyl, pyridyl and imidazolyl, optionally substituted as described above.

The term "substituted amino" refers to a group of the formula $-NZ_1Z_2$ wherein $Z_1$ is hydrogen, alkyl, or aryl-$(CH_2)_{p^-}$ and $Z_2$ is alkyl or aryl-$(CH_2)_{p^-}$ or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

The compounds of formula I can be prepared by coupling a compound of the formula

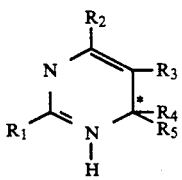

II with a compound of the formula

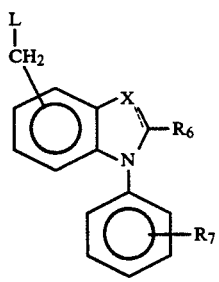

III (wherein L is a leaving group such as a halogen,

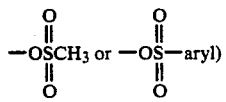

in the presence of a base, such as potassium carbonate, in an organic solvent such as dimethylformamide.

Compounds of formula II wherein $R_2$ is a halogen, and $R_3$ is $-CO_2R_{17}$ can be prepared by first reacting an amidine of the formula

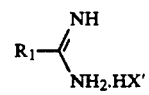

(wherein X' is a halogen) with an olefin of the formula

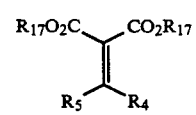

in an organic solvent, such as dimethylformamide, in the presence of a base, such as potassium carbonate to provide a pyrimidine of the formula

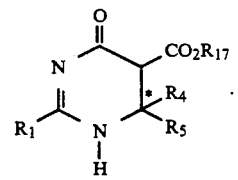

The pyrimidine of formula VI can thereafter be heated in the presence of a chlorinating agent such as phosphorous oxychloride to provide the intermediates of formula II where $R_2$ is chloro and $R_3$ is $-CO_2R_{17}$. Compounds of formula II where $R_2$ is a halogen other than chloro can be made in a similar fashion.

To provide the intermediates of formula II wherein $R_2$ is other than halogen, the amidine of formula IV can be reacted with an olefin of the formula

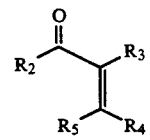

VII in the presence of a base for example, sodium bicarbonate, and in an organic solvent such as dimethylformamide to provide an intermediate of the formula

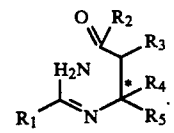

VIII

Intermediate VIII can thereafter be cyclized, e.g., by heating in the presence of an acid, such as p-toluenesulfonic acid, in an organic solvent, such as benzene or dimethylformamide, to provide compounds of formula II where $R_2$ is other than halogen.

Compounds of formula II, wherein $R_4$ and $R_5$ together with the carbon atom to which they are attached form a carbonyl group, can be prepared by reacting compounds of the formula

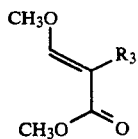

IX with an amidine of formula IV in the presence of a base such as sodium bicarbonate or sodium acetate.

Alternatively, compounds of formula II wherein $R_4$ and $R_5$ are a carbonyl group can be prepared by reacting a compound of the formula

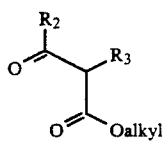

X with an amidine of formula IV in the presence of a base such as sodium bicarbonate or sodium acetate in a polar solvent such as ethanol or dimethylformamide.

Preferably, compounds of formula II wherein $R_4$ and $R_5$ together form a carbonyl group and $R_2$ and $R_3$ together form a fused aryl group, can be prepared by reacting anthranilamide with an acyl halide such as valeryl chloride ($R_1$=n-Bu) to form a compound of formula

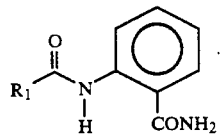

Xa

Compounds of formula Xa are then reacted in an organic solvent such as toluene with a base such as pyridine in the presence of a dehydrating agent such as molecular sieves to form the compounds of formula II.

Other dihydropyrimidines of formula II can be prepared by methods described in the literature, e.g., K. Atwal et al., *J. Org. Chem.*, Vol. 54, p. 5898 (1989) and references cited therein.

Compounds of formula III where X is

can be prepared by coupling a compound of the formula

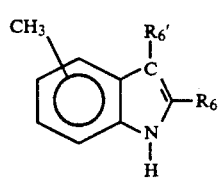

XI with a compound of the formula

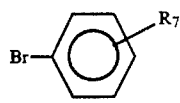

XII where Br is bromide in a polar solvent such as pyridine and in the presence of a catalyst such as copper oxice, to provide compounds of the formula

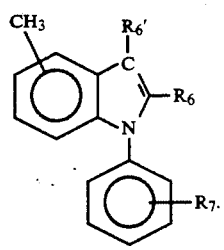

XIII

A leaving group, L, for example a halogen can be added by known methodology to provide compounds of the formula

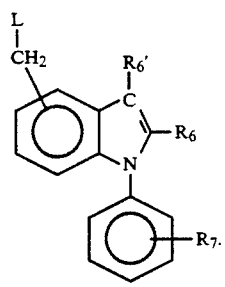

IIIa

Compounds of formula III where X is

or X is nitrogen may also be prepared by reacting a compound of the formula

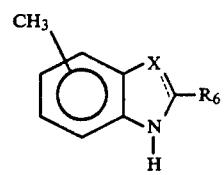

XIV with a compound of the formula

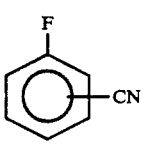

XV in the presence of a base such as potassium carbonate in an organic solvent such as dimethylformamide, to provide a compound of the formula

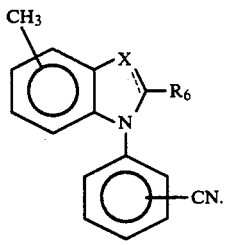

XVI

Compound XVI can thereafter be treated with a brominating agent such as N-bromosuccinimide and a radical initiator such as 2,2'-azobisisobutyronitrile, in an organic solvent such as carbon tetrachloride, to provide a compound of the formula

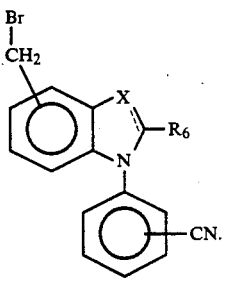

XVII

Intermediate XVII can be coupled with the pyrimidine of formula II to provide

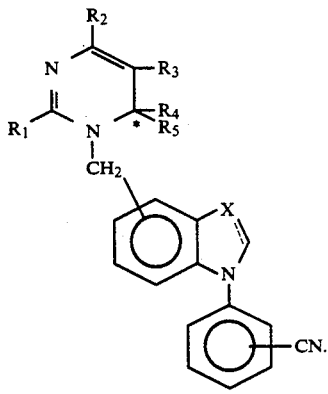

XVIII

Compounds of formula XVIII can then be reacted with an azide such as tributyltinazide to provide compounds of formula I wherein $R_7$ is

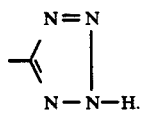

Compounds of formula I where $R_7$ is other than

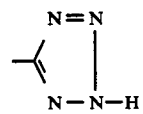

can be prepared using intermediate XII in place of compound XV above.

Compounds of formula XI can be prepared by known techniques such as those described in *J. Heterocyclic Chem.*, 25,1 (1988).

Compounds of formula XIV where X is nitrogen are prepared as described by Mathias et al., *Synthetic Communications*, 5, 461–469 (1975).

The compounds of formula I and I' can have an asymmetric center within the pyrimidine ring as represented by the asterisk (*). Also, any of the R groups can have an asymmetric center. Thus, the compounds of formula I can exist in diastereomeric forms or in mixtures thereof. The above-described processes can utilize racemates, enantiomers or diastereomers as starting materials. When diastereomeric products are prepared, they can be separated by conventional chromatographic or fractional crystallization methods.

When preparing the compounds of the instant invention wherein the substituent groups contain one or more reactive functionalities such as hydroxy, amino, tetrazolyl, carboxyl, mercapto or imidazolyl groups, it may be necessary to protect these groups during the reactions in which they are used. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of the present invention are those wherein $R_1$ is an alkyl of 3 to 5 carbons;

$R_2$ is hydrogen, alkyl, haloalkyl or chloro and $R_3$ is $-CO_2R_{17}$; or $R_2$ and $R_3$ form a fused aryl ring;

$R_4$ is hydrogen and $R_5$ is alkyl; or $R_4$ and $R_5$ together with the carbon atom to which they are attached form a carbonyl group;

$R_6$ is hydrogen or $-CO_2H$;

$R_7$ is ortho-tetrazolyl or $-CO_2H$;

X is $-N$; or

where $R_6'$ is hydrogen or $-CO_2H$; and the double bond is present.

Most preferred compounds of the present invention are those wherein $R_1$ is n-butyl;

$R_2$ is hydrogen, $-CF_3$ or chloro and $R_3$ is $-CO_2R_{17}$ or $R_2$ and $R_3$ form a fused aryl ring;

$R_4$ is hydrogen and $R_5$ is methyl; or $R_4$ and $R_5$ together with the carbon atom to which they are attached form a carbonyl group;

$R_6$ is hydrogen;

$R_7$ is ortho-tetrazolyl;

X is

where $R_6'$ is hydrogen; the double bond is present; and connection to the dihydropyrimidine group is via the 4-position of the indole.

The present compounds of formula I and I' inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment/prevention of congestive heart failure, cardiac hypertrophy, loss of cognitive function, renal failure and are useful for kidney transplant. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension or congestive heart failure. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian specie in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I and I' can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I or I' is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

2-Butyl-3-[[1-[2-(2H-tetrazol-5-yl)phenyl]-1H-indol-4-yl]methyl-4(3H)-quinazolinone, lithium salt

A. 2-(4-Methyl-1H-indol-1-yl)benzonitrile

4-Methyl-1H-indole (1.042 g, 7.94 mmol, 1.0 eq) was combined with 2-fluoro-benzonitrile (1.29 mL, 11.91 mmol, 1.5 eq) and potassium carbonate (2.195 g, 15.88 mmol, 2.0 eq) in DMF (7.94 mL, 1M) and heated at 150° C. for 4 hours. The reaction was then cooled to room temperature, diluted with water (20 mL), and extracted three times with ethyl acetate. The organic extracts were washed with water and aqueous saturated sodium chloride, dried over sodium sulfate, filtered through magnesium sulfate and concentrated. The residue was chromatographed on Merck silica gel (50 g) eluting with chloroform:hexane (1:3) followed by (1:1) to give the title compound (1.57 g, 85%).

B. 2-[2,3-Dibromo-4-(bromomethyl)-1H-indol-1-yl]benzonitrile

N-bromosuccinimide (3.615 g, 20.11 mmol, 3.0 eq) was added to a solution of the title A compound (1.557 g, 6.70 mmol, 1.0 eq) in carbon tetrachloride (134 mL, 0.05 M) and benzene (26.8 mL, 0.25 M) and the reaction was placed next to a bright lamp at room temperature for 3 hours. The mixture was then diluted with chloroform (134 mL, 0.05 M), cooled to 0° C., filtered and concentrated. The residue was chromatographed on Merck silica gel (100 g) eluting with hexane:chloroform (1:1) followed by (2:3) followed by (1:2) to give the title compound (2.268 g, 72%).

C. 2-[(1-Oxopentyl)amino]benzamide

Valeryl chloride (6.0 mL, 50 mmol) was added to a mixture of anthranilamide (6.8 g, 50 mmol) and triethylamine (7.0 mL, 50 mmol ) in tetrahydrofuran (100 mL) at 25° C. A rapid, exothermic reaction was observed, but no external cooling was required to prevent reflux. The mixture was stirred at ambient temperature for 19 hours, after which it was poured into excess aqueous sodium bicarbonate solution, extracted with ethyl acetate, dried (magnesium sulfate), and concentrated in vacuo. The residue was triturated with hexane/ether to give the title compound as a tan solid (9.9 g, 90%); m.p. 119°-120° C.

D. 2-Butyl-4(3H)-quinazolinone

A mixture of the title C compound (9.2 g, 42 mmol), toluene (200 mL) and pyridine (150 mL) was heated to reflux, after which molecular sieves (3 Å 100 mL) were added. The mixture was heated at reflux for 2 hours, more molecular sieves (100 mL) were added and reflux was continued for a total of 18 hours. The mixture was then filtered and the filtrate was concentrated in vacuo. The residue was dissolved in chloroform (500 mL), filtered again (millipore), and reconcentrated. The residue was triturated with hexanes to give the title compound as a white solid (6.8 g, 80%); m.p. 153°-155° C.

E. 2-[2,3-Dibromo-4-[2-butyl-4-oxo-3(4H)-quinazolinyl]-methyl]-1H-indol-1-yl]benzonitrile Tribromoindole (the title B compound; 3.56 g, 7.75 mmol) was added to a partial solution of quinazolinone (the title D compound; 1.54 g, 7.60 mmol) and potassium carbonate (1.58 g, 11.4 mmol) in 20 mL of dimethylformamide and the reaction mixture was stirred at 45° C. for 3 hours. Ethyl acetate (200 mL) was added and the organic solution was washed with water (2×), pH 4 buffer, brine, dried (sodium sulfate), filtered and concentrated in vacuo. Crude product was chromatographed through 200 g of Merck silica gel using a 2:8 ethyl acetate:hexane solvent system. The appropriate fractions were combined and concentrated in vacuo to yield 1.81 g (39.5%) of the title compound.

F.
2-[4-[[2-Butyl-4-oxo-3(4H)-quinazolinyl]-methyl]-1H-indol-1-yl]benzonitrile

The title E compound (1.8 g, 3 mmol) and triethylamine (0.8 mL, 5.7 mmol) were dissolved in 30 mL of a 2:1 toluene:ethanol mixture and hydrogenated for 50 minutes using 10% palladium on charcoal (0.2 g) as a catalyst. The reaction mixture was filtered through Celite, concentrated in vacuo and dissolved in 200 mL of methylene chloride. The organic solution was washed with water, pH 4 buffer, brine, dried (sodium sulfate), and concentrated in vacuo to yield 1.27 g (96%) of the title compound.

G.
2-Butyl-3-[[1-[2-(2H-tetrazol-5-yl)phenyl]-1H-indol-4-yl]methyl-4(3H)-quinazolinone, lithium salt Tributyltin azide (2.0 g, 5.7 mmol) and the title F compound (1.2 g, 2.8 mmol) were heated at 140° C. for 6 hours in 2 mL of xylene. The reaction mixture was diluted with 50 mL of a 2:1:50 methanol:acetic acid:chloroform solvent system and stirred overnight with 30 g of silica gel. The reaction mixture was concentrated in vacuo and chromatographed through 100 g Merck silica gel using the above solvent system. The appropriate fractions were combined and concentrated to yield 0.77 g of the title compound contaminated with tributyl tin byproduct. The title compound was dissolved in 2.5 mL of 1N lithium hydroxide and passed through 80 mL of HP-20 using a 25% acetone:water solvent system. The appropriate fractions were combined, concentrated in vacuo, dissolved in 30 mL of water, filtered through a millipore filter, and lyophilized. Because of poor lyophilization, the sample was redissolved in 300 mL of water, filtered through millipore and re-lyophilized to yield 0.44 g (31%) of the title compound as a white solid (m.p. >250° C.).

EXAMPLE 2
2-Butyl-3-[[1-[2-(2H-tetrazol-5-yl)phenyl]-1H-benzimidazol-4-yl]methyl]-4(3H)-quinazolinone, monolithium salt A. 4-Methyl-1H-benzimidazole 2,3 Diaminotoluene (675 mg, 5.53 mmol) was dissolved in 10 mL of dry tetrahydrofuran and triethylamine (0.77 mL, 5.53 mmol) was added. The mixture was cooled to 0° C. and 1,1-dichloromethyl methyl ether (0.50 mL, 5.53 mmol) was added and the reaction was allowed to warm to room temperature. After 20 hours, the reaction was quenched with sodium bicarbonate. The aqueous phase was extracted with ethyl acetate, dried over magnesium sulfate, filtered and the solvent removed to yield 730 mg (100%) of a brown solid.

B. 2-(4-Methyl-1H-benzimidazol-1-yl)-benzonitrile

The title A compound (133 mg, 1.01 mmol), 2-fluorbenzonitrile (164 μL, 1.51 mmol) and finely ground potassium carbonate (279 mg, 2.02 mmol) were combined in 1 mL of N,N-dimethylformamide (DMF) and heated to 80° C. After stirring for 20 hours, the DMF was removed in vacuo and the brown solid residue was partitioned between saturated sodium bicarbonate and ethyl acetate. The aqueous phase was extracted with ethyl acetate and the combined organic extracts were dried over magnesium sulfate, filtered and the solvent removed. The residue was purified by flash chromatography (20 g silica gel, eluted with 50% ethyl acetate, hexane) to provide 160 mg (68%) of a white solid.

C.
2-[4-(Bromomethyl)-1H-benzimidazol-1-yl]benzonitrile

The title B compound (71 mg, 0.30 mmol) was dissolved in 5 mL of 50% carbon tetrachloride and benzene. Azobisisobutyronitrile (10 mg, 0.06 mmol) and N-bromosuccinimide (65 mg, 0.36 mmol) were added and the mixture was heated to 75° C. for four hours. The solvent was removed and the residue was purified by flash chromatography (20 g silica gel eluted with 10% acetone, toluene) to yield 79 mg (84%) of a white solid; m.p. 135° C.(dec).

D. 2-Butyl-3-[[1-(2-cyanophenyl)-1H-benzimidazol-4-yl]methyl]-4(3H)-quinazolinone Finely ground potassium carbonate (0.90 g, 6.5 mmol) was added to a solution of the title D compound of Example 1 (1.05 g, 5.2 mmol) in 10.0 mL of DMF. The title C compound (1.56 g, 5.0 mmol) was then added to the stirring solution at room temperature, and reaction was stirred at room temperature overnight. 18 hours later, the reaction was diluted with methylene chloride and washed with saturated ammonium chloride and water. The organics were dried, concentrated and flash chromatographed on silica eluting with 80:15:5 hexane:acetone:isopropanol. The product was concentrated yielding 1.50 g (69%) of the title compound.

E.
2-Butyl-3-[[1-[2-(2H-tetrazol-5-yl)phenyl]-1H-benzimidazol-4-yl]methyl]-4(3H)-quinazolinone The title D compound (1.50 g, 3.46 mmol) and tributyltin azide (4.6 g, 13.84 mmol) were combined in xylene (7.0 mL) and heated at 110° C. overnight. 15 hours later, the reaction was cooled to room temperature and concentrated. Crude product was then flash chromatographed on silica gel eluting with 60:35:5 ethyl acetate: hexane:acetic acid to yield 1.43 g (87%) of the title compound.

F.
2-Butyl-3-[[1-[2-(2H-tetrazol-5-yl)phenyl-1H-benzimidazol-4-yl]methyl]-4(3H)-quinazolinone, monolithium salt 1.0M lithium hydroxide (12.0 mL, 12 mmol) was added to the title E compound (1.43 g, 3.0 mmol) and the reaction was diluted with approximately 5 mL of water. The reaction was then concentrated, dissolved in 60:40 water: methanol and placed on an HP-20 column. The column was eluted using 100% water, then increasing stepwise in 5% increments to 30% acetone, 70% water. Product eluted at 75:25 water:acetone. Product was passed through a millipore filter and lyophilized overnight to provide 1.20 g (83%) of white solid.

EXAMPLE 3

4-[(2-Butyl-4-oxo-3(4H)-quinazolinyl)methyl]-1-[2-(2H-tetrazol-5-yl)phenyl]-1H-indole-3-carboxylic acid, dilithium salt

A.
1-(2-Cyanophenyl)-4-methyl-1H-indole-3-carboxaldehyde

To a solution of oxalyl chloride in methylene chloride (2M, 4.52 mL, 9.041 mmol, 1.5 eq) at −20° C. was added dropwise a solution of DMF in methylene chloride (1N, 9.041 mL, 9.041 mmol, 1.5 eq). The reaction was warmed to 0° C. and stirred for 20 minutes, then cooled to −20° C. and the title A compound of Example 1 (1.40 g, 6.027 mmol, 1 eq) was added as a solid. After stirring at room temperature for 16 hours, the reaction mixture was cooled to 0° C. 50 mL of saturated sodium carbonate water solution was added and the mixture was stirred for 10 minutes. The mixture was extracted with methylene chloride three times. The extracts were washed with water, dried (magnesium sulfate) and concentrated to give the title compound (1.50 g, 96%). TLC:$R_f$=0.76, silica gel, methylene chloride:ethyl acetate (4:1), UV.

B. 1-(2-Cyanophenyl)-4-methyl-1H-indole-3-carboxylic acid

To the title A compound (1.55 g, 5.955 mmol, 1.0 eq) and sulfamic acid (2.024 g, 20.843 mmol, 3.5 eq) in tetrahydrofuran (45 mL, 0.46M) at 0° C., was added sodium chlorite (1.885 g, 20.843 mmol, 3.5 eq) in water (45 mL, 0.46M) dropwise. The reaction was then stirred at 0° C. for 30 minutes. Chloroform (100 mL) was added and the aqueous layer was extracted with chloroform. The extracts were washed with water, dried (magnesium sulfate), and concentrated to give the title compound. TLC:$R_f$=0.2, silica gel, methylene chloride:ethyl acetate (4:1), UV.

C. 1-(2-Cyanophenyl)-4-methyl-1H-indole-3-carboxylic acid, ethyl ester

The title B compound was dissolved in 200 mL methanol:ethyl ether (1:1) and cooled to 0° C. An excess solution of diazoethane in ethyl ether (prepared by treating N-ethyl-N'-nitro-N-nitrosoguanidine with ethyl ether/40% potassium hydroxide) was added and the reaction was stirred at 0° C. for 30 minutes. Magnesium sulfate was then added. Next, the mixture was filtered, and concentrated. The residue was chromatographed on silica gel eluting with a mixture of hexane in methylene chloride (1:4) to give the title compound (1.7 g, 65% for two steps). TLC:$R_f$=0.3, silica gel, methylene chloride, UV.

D.
4-(Bromomethyl)-1-(2-cyanophenyl)-1H-indole-3-carboxylic acid, ethyl ester A mixture of the title C compound (1000 mg, 3.286 mmol, 1.0 eq), N-bromosuccinimide (626 mg, 3.516 mmol, 1.07 eq), 2,2'-azobisisobutyronitrile (30 mg, 3% by wt.) and carbon tetrachloride (55 mL, 0.06M) was refluxed for 3 hours. After cooling to room temperature, the solvent was evaporated in vacuo. The residue was chromatographed on silica gel eluting with hexane and methylene chloride (1:1) to give the title compound (1040 mg, 83%). TLC:$R_f$=0.4, silica gel, methylene chloride, UV.

E.
4-[(2-Butyl-4-oxo-3(4H)-quinazolinyl)methyl]-1-(2-cyanophenyl)-1H-indole-3-carboxylic acid, ethyl ester A mixture of the title D compound (1075 mg, 2.805 mmol, 1 eq), the title D compound of Example 1 (624 mg, 3.086 mmol, 1.1 eq), potassium carbonate (427 mg, 3.086 mmol, 1.1 eq) and DMF (5.6 mL, 0.5M) was stirred at room temperature for 16 hours. 10 mL water was added and the reaction was extracted with methylene chloride. The extracts were washed with water, then dried (magnesium sulfate) and concentrated. The residue was chromatographed on silica gel eluting with ethyl acetate in methylene chloride (1:100) to give the title compound (776 mg, 55%). TLC:$R_f$=0.6, silica gel, ethyl acetate:methylene chloride (1:10), UV.

F.
4-[(2-Butyl-4-oxo-3(4H)-quinazolinyl)methyl]-1-[2-(2H-tetrazol-5-yl)phenyl]-1H-indole-3-carboxylic acid, dilithium salt A mixture of the title E compound (774 mg, 1.534 mmol, 1 eq), tributyltin azide (1528 mg, 4.602 mmol, 3 eq) and xylene (19 mL, 0.08M) were heated at 120° C. for 32 hours. Additional tributyltin azide (255 mg, 0.767 mmol, 0.5 eq) was added after 28 hours. The mixture was concentrated and the residue was chromatographed on silica gel eluting with acetone to give an intermediate.

The intermediate was dissolved in 9.2 mL methanol. 1N lithium hydroxide water solution (9.2 mL, 9.2 mmol, 6 eq) was added and stirred at 42° C. for a total of 38 hours. At 20 hours, additional 1N lithium hydroxide (3.1 mL, 3.1 mmol, 2 eq) was added. Part of the solvent was evaporated under vacuum. 150 mL of water was added and the aqueous was washed with ethyl ether. The aqueous solution was concentrated and chromatographed on HP-20 eluting with acetone in water (5 to 15%) to give the title compound as a white solid (710 mg, 87%). TLC:$R_f$=0.22, silica gel, chloroform:methanol:acetic acid (10:2.5:0.04), UV.

What is claimed is:

1. A compound of the formula

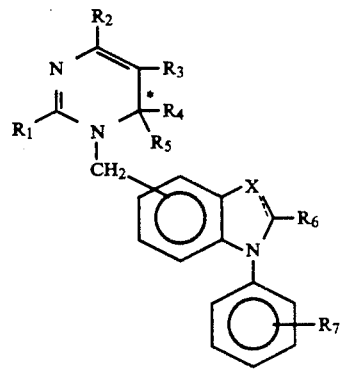

or its isomer

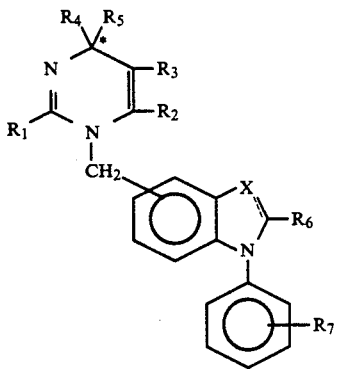

or a pharmaceutically acceptable salt thereof;
wherein
X is —N— or

when X is —N—, the double bond is always present;

R₁ is alkyl, alkenyl or alkynyl or an alkyl, alkenyl or alkynyl group substituted with F or —CO₂R₈; cycloalkyl; (cycloalkyl)alkyl of 4 to 10 carbon atoms; (cycloalkyl)alkenyl or (cycloalkyl)alkynyl of 5 to 10 carbon atoms; —NR₁₁R₁₂; —(CH₂)ₘZ(CH₂)ₙR₁₄; benzyl or benzyl substituted with 1 or 2 halogens, alkoxy of 1 to 4 carbon atoms, alkyl of 1 to 4 carbon atoms, haloalkyl or nitro; —SR₁₅; or —OR₁₅;

R₂ is hydrogen, —CN, —OR₁₅, —SR₁₅, —COR₁₅, R₁₆, (R₁₆O)alkyl, (R₁₆S)alkyl, —CO₂R₁₇ or (substituted amino)alkyl;

R₃ is —CN, —NO₂,

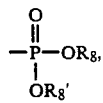

—CONR₁₁R₁₂, (R₁₅OCO)alkyl, (R₁₆O)alkyl, (R₁₆S)alkyl, (R₁₆CO)alkyl, —CO₂R₁₇, R₁₈, —COR₁₈, —SO₂R₁₈ or CR₁₈OC)alkyl; or R₂ and R₃ taken together are

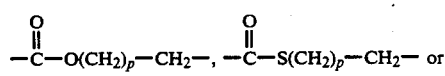

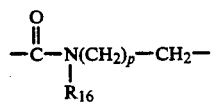

to form a 5- to 7-membered ring with the carbon atoms to which they are attached; or R₂ and R₃ taken together with the carbon atoms to which they are attached form an aryl or heterocyclo group;

R₄ and R₅ are independently selected from hydrogen, alkyl, alkenyl, alkynyl, aryl, arylalkyl, cycloalkyl, (cycloalkyl)alkyl, heterocyclo, (heterocyclo)alkyl, haloalkyl or —CO₂R₈; or R₄ and R₅ taken together with the carbon atom to which they are attached form a 5- to 7-membered carbocyclic ring which may have another 5- to 7-membered carbocyclic ring fused thereto; or R₄ and R₅ together with the carbon atom to which they are attached form a carbonyl or a thiocarbonyl group;

R₆ and R₆' are independently selected from hydrogen, alkyl, aryl, cycloalkyl, arylalkyl, haloalkyl,

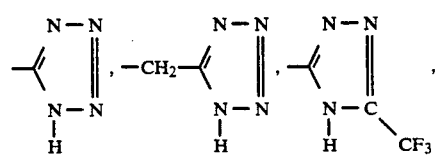

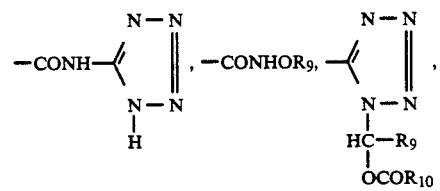

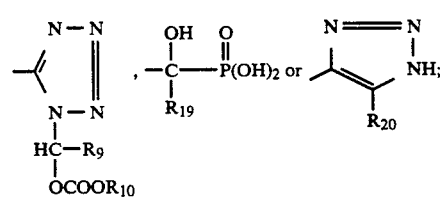

R₇ is an acid moiety such as hydrogen,

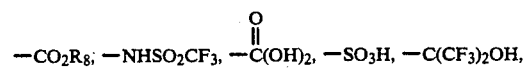

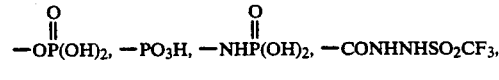

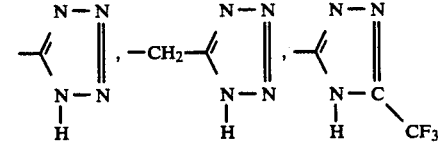

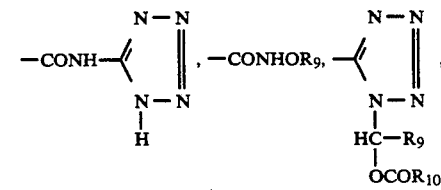

-continued

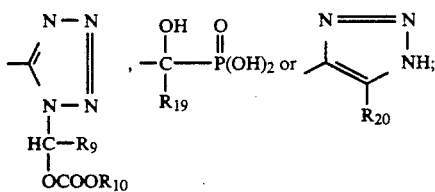

$R_8$ and $R_8'$ are independently hydrogen, alkyl, perfluoroalkyl of 1 to 8 carbon atoms, cycloalkyl of 3 to 6 carbon atoms, phenyl, benzyl,

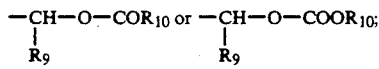

$R_9$ is hydrogen, alkyl, aryl, arylalkyl or cycloalkyl;
$R_{10}$ is alkyl, aryl, alkylaryl, arylalkyl or cycloalkyl;
$R_{11}$ and $R_{12}$ are independently hydrogen, alkyl of 1 to 6 carbon atoms, benzyl, α-methylbenzyl, or taken together with the nitrogen atom to which they are attached form a ring of the formula

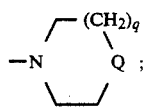

$R_{13}$ is hydrogen, alkyl of 1 to 6 carbon atoms, cycloalkyl of 3 to 6 carbon atoms, phenyl or benzyl;
$R_{14}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or —$CO_2R_8$;
$R_{15}$ is alkyl, alkenyl, alkynyl, aryl, arylalkyl, cycloalkyl, (cycloalkyl)alkyl, heterocyclo, (heterocyclo)alkyl or haloalkyl;
$R_{16}$ is hydrogen, alkyl, alkenyl, alkynyl, aryl, arylalkyl, cycloalkyl, (cycloalkyl)alkyl, heterocyclo, (heterocyclo)alkyl or haloalkyl;
$R_{17}$ is hydrogen, alkyl, alkenyl, alkynyl, perfluoroalkyl of 1 to 8 carbon atoms, cycloalkyl, aryl, arylalkyl, (cycloalkyl)alkyl, heterocyclo, (heterocyclo)alkyl, haloalkyl,

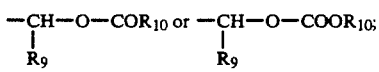

$R_{18}$ is aminoalkyl, (substituted amino)alkyl; or $R_{16}$;
$R_{19}$ is hydrogen, alkyl of 1 to 5 carbon atoms or phenyl;
$R_{20}$ is —CN, —$NO_2$ or —$CO_2R_8$;
Q is —$CH_2$, —O—, or —$NR_9$;
Z is —O—, —S— or —$NR_{13}$;
m is an integer of 1 to 5;
n is an integer of 1 to 5;
p is 0, or the integer 1 to 2;
q is 0, or the integer; and
wherein "alkyl" refers to both straight and branched chain groups having 1 to 10 carbon atoms;
"alkenyl" and "alkynyl" refer to both straight and branched chain groups having 2 to 10 carbon atoms;

"cycloalkyl" refers to groups having 3 to 8 carbon atoms;
"substituted amino" refers to a group of the formula —$NZ_1Z_2$ wherein $Z_1$ is hydrogen, alkyl, or aryl-$(CH_2)_p$- and $Z_2$ is alkyl or aryl-$(CH_2)_p$- or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy;
"aryl" refers to phenyl or naphthyl optionally substituted with substituents selected from halogen, alkyl, alkoxy, carboxy, alkylthio, hydroxy, alkanoyl, nitro, amino, alkylamino, dialkylamino or trifluoromethyl groups; and
"heterocyclo" refers to fully saturated or unsaturated rings of 5 to 6 atoms containing one to four nitrogen atoms, or one oxygen atom, or one sulfur atom, or one oxygen atom and one or two nitrogen atoms, or one sulfur atom and one or two nitrogen atoms optionally substituted with a substituent selected from alkyl of 1 to 4 carbons, carboxy, alkoxy of 1 to 4 carbons and alkylthio of 1 to 4 carbons on an available carbon; bicyclic rings wherein said five or six membered ring containing oxygen, sulfur or nitrogen atoms is fused to a benzene ring, optionally substituted with a substituent selected from alkyl of 1 to 4 carbons, carboxy, alkoxy of 1 to 4 carbons and alkylthio of 1 to 4 carbons on an available carbon.

2. The compound as recited in claim 1 wherein
$R_1$ is an alkyl of 3 to 5 carbons;
$R_2$ is hydrogen, alkyl, haloalkyl or chloro and $R_3$ is —$CO_2R_{17}$; or $R_2$ and $R_3$ form a fused aryl ring;
$R_4$ is hydrogen and $R_5$ is alkyl; or $R_4$ and $R_5$ together with the carbon atom to which they are attached form a carbonyl group;
$R_6$ is hydrogen or —$CO_2H$;
$R_7$ is Ortho-tetrazolyl or —$CO_2H$:
X is —N; or

where $R_6'$ is hydrogen or —$CO_2H$; and the double bond is present.

3. The compound as recited in claim 1 wherein
$R_1$ is n-butyl;
$R_2$ is hydrogen, —$CF_3$ or chloro and $R_3$ is —$CO_2R_{17}$; or $R_2$ and $R_3$ form a fused aryl ring;
$R_4$ is hydrogen and $R_5$ is methyl; or $R_4$ and $R_5$ together with the carbon atom to which they are attached form a carbonyl group;
$R_6$ is hydrogen;
$R_7$ is ortho-tetrazolyl;
X is

where $R_6'$ is hydrogen; the double bond is present; and connection to the dihydropyrimidine group is via the 4-position of the indole.

4. The compound as recited in claim 1 having the name 2-Butyl-3-[[1-[2-(2H-tetrazol-5-yl)phenyl]-1H-indol-4-yl]methyl-4(3H)-quinazolinone, or a pharmaceutically acceptable salt thereof.

5. The compound as recited in claim 1 having the name 2-Butyl-3-[[1-[2-(2H-tetrazol-5-yl)phenyl]-1H-benzimidazol-4-yl]methyl]-4(3H)-quinazolinone, or a pharmaceutically acceptable salt thereof.

6. The compound as recited in claim 1 having the name 4-[(2-Butyl-3,4-dihydro-4-oxo-3-quinazolinyl)methyl]-1-[2-(2H-tetrazol-5-yl)phenyl]-1H-indole-3-carboxylic acid, or a pharmaceutically acceptable salt thereof.

7. A pharmaceutical composition comprising the compound recited in claim 1 and a pharmaceutically acceptable carrier.

8. A method for treating hypertension comprising administering to a mammalian specie in need thereof a therapeutically effective amount of the composition of claim 7.

9. A method for treating congestive heart failure comprising administering to a mammalian specie in need thereof a therapeutically effective amount of the composition of claim 7.

10. A method for preventing cardiac hypertrophy comprising administering to a mammalian specie in need thereof a therapeutically effective amount of the composition of claim 7.

* * * * *

UNITED STATES PATENT AND TRADEMARK OFFICE
CERTIFICATE OF CORRECTION

PATENT NO. : 5,212,177
DATED : May 18, 1993
INVENTOR(S) : M.A. Poss et al.

It is certified that error appears in the above-identified patent and that said Letters Patent is hereby corrected as shown below:

In Claim 1, Column 18, Lines 15 and 48,

" $-\overset{O}{\underset{\|}{C}}(OH)_2,$ " should be -- $-O\overset{O}{\underset{\|}{S}}(OH)_2,$ -- .

Signed and Sealed this

Twentieth Day of September, 1994

BRUCE LEHMAN

Attest:

*Attesting Officer*     *Commissioner of Patents and Trademarks*